US010362952B2

(12) United States Patent
Basu et al.

(10) Patent No.: US 10,362,952 B2
(45) Date of Patent: Jul. 30, 2019

(54) STABILIZED SPINE ELECTROPHYSIOLOGIC CATHETER

(71) Applicant: Biosense Webster (Israel) Ltd., Yokneam (IL)

(72) Inventors: Shubhayu Basu, Anaheim, CA (US); Mario A. Solis, Rancho Cucamonga, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 296 days.

(21) Appl. No.: 14/965,745

(22) Filed: Dec. 10, 2015

(65) Prior Publication Data

US 2017/0165000 A1    Jun. 15, 2017

(51) Int. Cl.
*A61B 5/042* (2006.01)
*A61B 18/14* (2006.01)
*A61B 5/00* (2006.01)
*A61B 18/00* (2006.01)

(52) U.S. Cl.
CPC .......... *A61B 5/0422* (2013.01); *A61B 5/6858* (2013.01); *A61B 5/6859* (2013.01); *A61B 18/1492* (2013.01); *A61B 2018/00267* (2013.01); *A61B 2018/00351* (2013.01); *A61B 2018/00577* (2013.01); *A61B 2018/00642* (2013.01); *A61B 2018/00839* (2013.01); *A61B 2505/05* (2013.01)

(58) Field of Classification Search
CPC ... A61B 5/0422; A61B 5/6858; A61B 5/6859; A61B 18/1492
See application file for complete search history.

(56) References Cited

U.S. PATENT DOCUMENTS

| 5,345,936 | A | * | 9/1994 | Pomeranz | A61B 5/0422 600/374 |
| 5,391,199 | A | | 2/1995 | Ben-Haim | |
| 5,575,810 | A | * | 11/1996 | Swanson | A61B 18/1492 607/119 |

(Continued)

FOREIGN PATENT DOCUMENTS

| WO | 96/05768 | 2/1996 |
| WO | 2008084239 A2 | 7/2008 |

(Continued)

OTHER PUBLICATIONS

European Search Report from corresponding European Patent Application 16203105.8, dated Apr. 10, 2017, pp. 1-9.

*Primary Examiner* — Lee S Cohen
(74) *Attorney, Agent, or Firm* — Dergosits & Noah LLP; Todd A. Noah

(57) ABSTRACT

A catheter for diagnosing and ablating tissue is disclosed that has a stabilized spine electrode assembly. The stabilized spine electrode assembly has at least two spines secured to the catheter body at their proximal ends and at least one tether, secured between locations distal of the proximal ends of adjacent spines. The spines have a collapsed arrangement in which the spines are arranged generally along a longitudinal axis of the catheter body and an expanded arrangement in which at least a portion of each spine bows radially outwards from the longitudinal axis and the at least one tether exerts tension on the adjacent spines.

17 Claims, 5 Drawing Sheets

(56) References Cited

U.S. PATENT DOCUMENTS

| | | | |
|---|---|---|---|
| 5,702,438 A * | 12/1997 | Avitall | A61B 18/1492 |
| | | | 600/374 |
| 5,772,590 A | 6/1998 | Webster, Jr. | |
| 6,064,905 A | 5/2000 | Webster et al. | |
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,669,693 B2 * | 12/2003 | Friedman | A61B 18/1492 |
| | | | 606/41 |
| 6,690,963 B2 | 2/2004 | Ben-Haim | |
| 6,748,255 B2 | 6/2004 | Fuimaono et al. | |
| 6,961,602 B2 | 11/2005 | Fuimaono et al. | |
| 6,973,340 B2 | 12/2005 | Fuimaono et al. | |
| 7,615,049 B2 * | 11/2009 | West | A61B 18/1492 |
| | | | 606/41 |
| 8,447,377 B2 * | 5/2013 | Harley | A61B 5/0422 |
| | | | 29/825 |
| 8,818,501 B2 * | 8/2014 | Machado | A61N 1/36114 |
| | | | 607/2 |
| 9,101,342 B2 * | 8/2015 | Saleh | A61B 10/04 |
| 9,119,634 B2 * | 9/2015 | Gelbart | A61B 5/028 |
| 2002/0065455 A1 | 5/2002 | Ben-Haim et al. | |
| 2003/0018330 A1 * | 1/2003 | Swanson | A61B 18/1492 |
| | | | 606/41 |
| 2003/0120150 A1 | 6/2003 | Govari | |
| 2004/0068178 A1 | 4/2004 | Govari | |
| 2006/0106298 A1 * | 5/2006 | Ahmed | A61B 5/0422 |
| | | | 600/381 |
| 2009/0171274 A1 | 7/2009 | Harlev et al. | |
| 2014/0194716 A1 * | 7/2014 | Diep | A61B 5/6859 |
| | | | 600/374 |
| 2015/0208937 A1 * | 7/2015 | Bullinga | A61B 5/0408 |
| | | | 600/424 |
| 2017/0035496 A1 * | 2/2017 | Nagale | A61B 18/1485 |
| 2017/0035497 A1 * | 2/2017 | Nagale | A61B 18/1492 |

FOREIGN PATENT DOCUMENTS

| | | |
|---|---|---|
| WO | 2008141150 A2 | 11/2008 |
| WO | 2011143468 A2 | 11/2011 |
| WO | 2015130824 A1 | 9/2015 |

* cited by examiner

STABILIZED SPINE ELECTROPHYSIOLOGIC CATHETER

FIELD OF THE PRESENT DISCLOSURE

This invention relates to electrophysiologic (EP) catheters, in particular, EP catheters for mapping electrical signals and/or ablating tissue in the heart.

BACKGROUND

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector. Mapping the activation front and conduction fields aids the physician in identifying and diagnosing abnormalities, such as ventricular and atrial tachycardia and ventricular and atrial fibrillation, that result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated (if it is functioning abnormally) or otherwise treated so as to restore the normal function of the heart insofar as is possible. As an illustration, cardiac arrhythmias including atrial fibrillation, may occur when regions of cardiac tissue abnormally conduct electric signals to adjacent tissue, thereby disrupting the normal cardiac cycle and causing asynchronous rhythm. Procedures for treating arrhythmia include disrupting the origin of the signals causing the arrhythmia, as well as disrupting the conducting pathway for such signals, such as by forming lesions to isolate the aberrant portion. Thus, by selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

A number of advantages may be obtained by providing a catheter having multiple electrodes to allow for mapping larger regions and/or for creating a plurality of lesions either simultaneously or without the need to reposition the catheter. One suitable configuration described in commonly assigned U.S. Pat. No. 6,961,602, which is herein incorporated by reference, employs a catheter having a multiray electrode assembly formed by a plurality of spines each carrying one or more diagnostic or ablation electrodes. The assembly has two or more spines, each having a proximal end attached at the distal end of the catheter body and a free distal end. Another configuration that has been employed is known as a basket-shaped electrode assembly. Examples are described in commonly assigned U.S. Pat. Nos. 5,772,590, 6,748,255 and 6,973,340, the entire disclosures of each of which are incorporated herein by reference. Basket catheters also employ a plurality of spines, which are connected at their distal end as well as the proximal end. In either configuration, the spines may be arranged in an expanded arrangement wherein at least a portion of each spine extends radially outwardly from the catheter body or in a collapsed arrangement wherein each spine is disposed generally along the longitudinal axis of the catheter body. The collapsed arrangement facilitates advancing the electrode assembly to the desired location in the patient's body, such as through the vasculature in a percutaneous approach. When the electrode assembly assumes the expanded arrangement, one or more of the electrodes on the spines are brought into contact with tissue to allow for measurement of electrical signals and/or ablation of tissue.

By employing multiple spines, these electrode assemblies are adapted to provide an array of electrodes to occupy a three dimensional space defined by the anatomy of the patient, such as a chamber of the heart or an ostium vessel for example. Generally, it is desirable for the spines to be distributed evenly when expanded to provide uniform coverage of the electrode array over the space in which the spines are deployed. Alternatively, it may be desirable to distribute the spines in an uneven, but defined configuration in order to concentrate the electrodes at one or more regions of the space. However, conventional multiple spine electrode assemblies may not deploy with the spines in the intended configuration. For example, in a multiray electrode assembly, the spines are secured in relation to each other only at the proximal end, while in a basket-shaped electrode assembly, they are secured only at their proximal and distal ends. As such, the spines may not assume their intended radial distribution, particularly at locations that are farther away from the secured ends. Notably, the spines may bunch together more closely or may splay apart to a greater degree than desired. The tendency of the multiple spine electrode assemblies to assume such suboptimal distributions may be exacerbated by irregularities in a patient's anatomy.

Accordingly, there is a need for a multiple spine electrode assembly that helps maintain a desired relationship between the spines when deployed in their expanded arrangement. Similarly, there is a need for a multiple spine electrode assembly in which the spines are stabilized with respect to each other. The techniques of this disclosure as described in the following materials satisfy these and other needs.

SUMMARY

The present disclosure is directed to a catheter with an elongated catheter body having proximal and distal ends and a stabilized spine electrode assembly mounted at the distal end of the catheter body and comprising at least two spines and at least one tether, each spine having a proximal end attached at the distal end of the catheter body, wherein the at least one tether may be secured to locations distal of the proximal ends of adjacent spines and wherein each spine has a collapsed arrangement in which the spines are arranged generally along a longitudinal axis of the catheter body and an expanded arrangement in which at least a portion of each spine bows radially outwards from the longitudinal axis and the at least one tether exerts tension on the adjacent spines.

In one aspect, the stabilized spine electrode assembly may have at least three spines and at least two tethers, wherein the at least two tethers may be secured to locations distal of the proximal ends of at least one spine and each adjacent spine. Each spine may be secured to adjacent spines by at least one tether. Further, the tethers may be configured to maintain a desired radial distribution of the spines relative to each other when in the expanded arrangement. For example, the tethers may be configured to maintain an even radial distribution of the spines relative to each other when in the expanded arrangement.

In one aspect, the stabilized spine electrode assembly may have at least two tethers, wherein the at least two tethers are secured between adjacent spines.

In one aspect, the stabilized spine electrode assembly may have at least two tethers, wherein the at least two tethers are secured to one location on one spine and to a plurality of locations on an adjacent spine.

In one aspect, at least one tether may be secured to a proximal third of a spine, an intermediate third of a spine and/or a distal third of a spine.

In one aspect, the stabilized spine electrode assembly may have at least three spines with distal ends secured to each other to form a basket-shaped electrode assembly. Each spine may be secured to adjacent spines by at least one tether. For example, the tethers may be secured between equatorial locations of the spines.

In one aspect, the tether(s) may be a polymeric fiber. Depending on the embodiment, the tether(s) may be compliant or relatively noncompliant.

This disclosure also includes a method for treatment that involves providing a catheter with an elongated catheter body having a proximal end, a distal end and a stabilized spine electrode assembly mounted at the distal end of the catheter body and comprising at least two spines and at least one tether, each spine having at least one electrode and a proximal end attached at the distal end of the catheter body, wherein the at least one tether is secured to locations distal of the proximal ends of adjacent spines. The distal end of the catheter with the stabilized spine electrode assembly may be advanced to a desired region within a patient with each spine in a collapsed arrangement wherein the spines are arranged generally along a longitudinal axis of the catheter body. The stabilized spine electrode assembly may be caused to assume an expanded arrangement in which at least a portion of each spine bows radially outwards from the longitudinal axis and the at least one tether exerts tension on the adjacent spines so that at least one electrode is in contact with tissue.

In one aspect, electrical signals may be received from the at least one electrode in contact with tissue.

In one aspect, radio frequency energy may be delivered to the at least one electrode in contact with tissue to form a lesion.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a", "an" and "the" include plural referents unless the content clearly dictates otherwise.

As will be described herein, this disclosure is directed to a catheter having a stabilized spine electrode assembly. The electrode assembly features multiple spines having an expanded arrangement with a desired distribution of the spines in relation to each other. One or more tethers may be secured to location(s) intermediate the proximal and distal ends of adjacent spines. Each tether constrains the spines from moving apart from each other, thereby stabilizing the electrode assembly.

Figure 1:
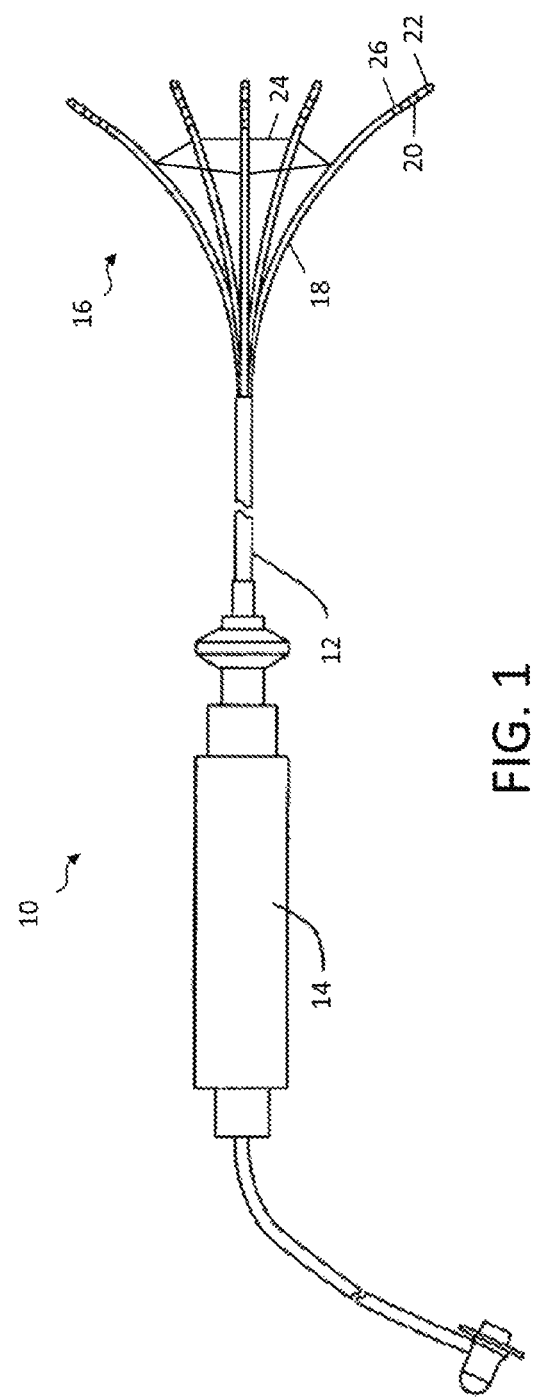
FIG. 1 is a top plan view of a catheter of the present invention, with a multiray stabilized spine electrode assembly, according to one embodiment.

To help illustrate aspects of this disclosure, an exemplary embodiment of an electrophysiologic catheter with a multiple spine electrode assembly is shown schematically in FIG. 1. Catheter 10 comprises an elongated catheter body 12 having proximal and distal ends, a control handle 14 at the proximal end of the catheter body 12, and a stabilized spine electrode assembly 16 comprising a plurality of spines 18 mounted at the distal end of the catheter body 12 radiating outwards in a multiray configuration. Each spine 18 may carry one or more electrodes, such as ring electrodes 20 that may be located at any location along the length of spine 16 and cup electrodes 22 that may be located at the distal tip of spine 18. As will be described in further detail below, tethers 24 are secured to intermediate locations between the proximal and distal ends of radially adjacent spines 18 to stabilize them with respect to each other. In the embodiment shown, a single tether 24 is employed between adjacent spines 18, but any number may be used to obtain a desired degree of stability.

Tethers 24 may be formed from any suitable material, such as biocompatible polymers. In one aspects, tethers 24 may be formed from polymeric fibers of materials such as polyamides, polyesters, aramids, polyethylenes, polyurethanes and others. Tethers 24 may be secured to spines 18 using any suitable technique, including without limitation adhesives, mechanical fasteners, heat bonding and the like. The location at which tethers 24 are secured to spines 18 may be tailored to achieve any combination of desired characteristics. For example, attachment relatively closer to the proximal ends of spines 18 may increase the freedom of the distal portions of the spines 18 to conform to the surrounding tissue. Conversely, attachment relatively closer to the distal ends of spines 18 may afford increased stability. As such, in some embodiments, tethers 24 may be secured between locations within a proximal third of the spine length on adjacent spines 18 to provide a balance between increased stability and freedom of the distal ends of spines 18. In still further embodiments, tethers 24 may be secured between locations within a distal third of the spine length on adjacent spines 18 to further enhance stability with reduced freedom of the distal ends of spines 18. Thus, corresponding tethers 24 between different adjacent pairs of spines 18 may be secured to locations that are relatively equivalent in the longitudinal direction. In alternative embodiments, the locations at which a tether 24 is secured to adjacent spines 18 may be offset with respect to each other, such as by running from a proximal location to a distal location or by running from a proximal or distal location to an intermediate location.

Depending on the embodiment, tethers 24 may be formed form relatively compliant or non-compliant materials. Compliant materials may be desirable in embodiments in which the overall size or shape of stabilized spine electrode assembly 16 is adjustable. As described below, some embodiments of stabilized spine electrode assembly 16 may be manually expandable to change its configuration to help conform to the tissue in the region in which it is deployed. As such, compliant tethers 24 may impart a stabilizing force to spines 18 over a range of relative distances between adjacent spines. For example, in a first configuration of stabilized spine electrode assembly 16, a pair of adjacent spines may be a first distance apart that is approximately the native length of tether 24. As such, each spine 18 may be constrained by the resilience of tether 24 so that it is stabilized with respect to its adjacent spines. Stabilized spine electrode assembly 16 may then be expanded or its shape otherwise changed to assume a second configuration in which the pair of adjacent spines are now a second distance apart, which is greater than the first distance. A suitably compliant tether 24 may deform to accommodate the greater distance, while still providing the stabilizing tension with respect to the adjacent spines. Alternatively, tether 24 may be formed from a relatively noncompliant material when it is desired that spines 18 maintain a single defined distance between each other when in the expanded arrangement. As used herein, the term "compliant" means the tether may be deformed by forces experience when the spines assume an expanded arrangement and the term "relatively noncompliant" means the tether does not substantially deform when the spines assume an expanded arrangement. Further, whether compliant or noncompliant, tether 24 may be sufficient flexible to allow spines 18 to assume the collapsed configuration in which they are generally aligned with the longitudinal axis of catheter 10.

Catheter body 12 comprises an elongated tubular construction having a single, axial or central lumen but can optionally have multiple lumens along all or part of its length if desired. Catheter body 12 is flexible, i.e., bendable, but substantially non-compressible along its length. Catheter body 12 can be of any suitable construction and made of any suitable material, such as by using an outer wall of polyurethane or PEBAX® (polyether block amide). The wall may have an imbedded braided mesh of stainless steel or the like, as is generally known in the art, to increase torsional stiffness of the catheter body 12 so that, when the control handle 14 is rotated, the distal end of the catheter body 12 will rotate in a corresponding manner The length of the catheter body 12 is not critical, but may range from about 90 cm to about 120 cm, such as about 110 cm. The outer diameter of the catheter body 12 is also not critical, but generally be adapted to present an outer diameter sufficient to accommodate the construction of stabilized spine electrode assembly 16 and any associated leads, irrigation lumens, puller wires, position or other sensors and the like while retaining an insertion profile that allows advancement through the patient's vasculature. In some embodiments, catheter body 12 may be about 10 french or less, such as 8 french or 7 french. Likewise, the thickness of the outer wall of catheter body 12 is not critical but may be thin enough provide a lumen or lumens of sufficient size. An example of a catheter body construction suitable for use in connection with the present invention is described and depicted in U.S. Pat. No. 6,064,905, the entire disclosure of which is incorporated herein by reference.

In the depicted embodiment, stabilized spine electrode assembly 16 comprises five spines 18. Each spine 18 has a proximal end attached at the distal end of the catheter body 12 and a free distal end, i.e., the distal end is not attached to any of the other spines, to the catheter body, or to any other structure that confines movement of the distal end. Each spine 14 may have an internal strut or other structural member comprising a metal or plastic material having resiliency characteristics that allow the spines 18 to assume their expanded and collapsed arrangements. Spine 18 may also have a non-conductive material covering the internal struts, such as a biocompatible plastic tubing, such as a polyurethane or polyimide tubing. Stabilized spine electrode assembly 16 may be a discrete element that is joined to catheter body 12 or may comprise an extension of catheter body 12. Stabilized spine electrode assembly 16 may be of a known fixed length.

As will be recognized by one skilled in the art, the number of spines 18 may vary as desired depending on the particular application, so that the catheter 10 has at least two spines, and may have three or more spines up to twelve or more. Spines 18 are moveable between an expanded arrangement, wherein, for example, each spine extends radially outwardly from the catheter body 12, or spines 18 may be arranged in a collapsed arrangement, wherein, for example, each spine is disposed generally along a longitudinal axis of the catheter body 12 so that the spines are capable of fitting within a lumen of a guiding sheath, as discussed further below.

As noted, each spine 18 carries at least one electrode mounted along its length, preferably at or near its distal end. In the depicted embodiment, cup electrode 22 is mounted on a distal end and ring electrodes 20 are mounted along the length of spines 18 on the non-conductive covering. As desired, ring electrodes 20 and/or cup electrodes 22 may be configured as unipolar, bipolar or both and may be diagnostic electrodes, ablation electrodes, reference electrodes or others. One or more spines 18 may also include position sensor 26, which may be used to help determine the orientation or location of spines 18 and/or stabilized spine electrode assembly 16 as described below.

In some embodiments, electrodes 20 and/or 22 may have perforations to allow for the delivery of irrigation fluid to the treatment site to help manage the temperature of the tissue be ablated. During delivery of RF current to each electrode 20, heating of the tissue occurs due to its electrical resistance. Heating the tissue causes cellular destruction in the target tissue that results in the formation of the non-conducting lesion that is intended to disrupt the influence of aberrant electrical signals. However, overheating the tissue may cause the undesirable formation of char and coagulum or may result in steam pops when liquid is heated beyond its boiling point, which in turn may create craters or perforations in the heart tissue. Correspondingly, irrigation at the ablation site may provide benefits including cooling of the electrode and tissue to prevent overheating of tissue. Additionally, spines 18 may also have thermocouple or other suitable temperature sensor to assess tissue temperature during an ablation procedure for avoiding such adverse occurrences and to help adjust the flow of irrigation fluid to prevent or minimize overheating.

Figure 2:
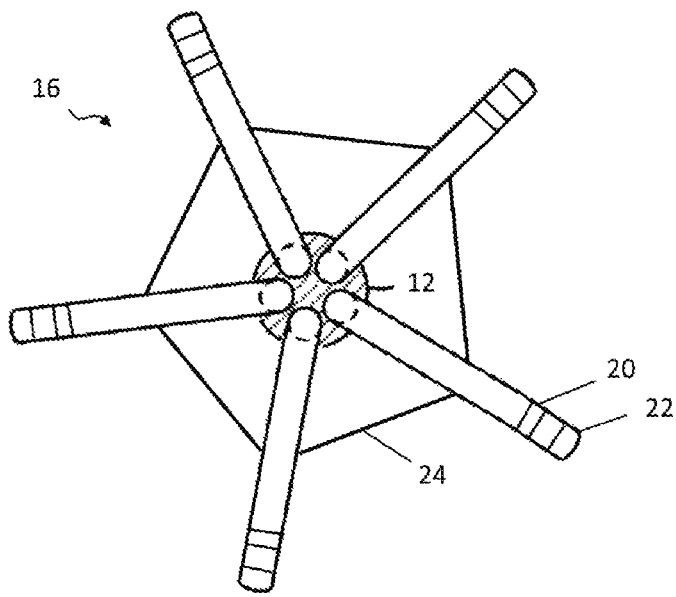
FIG. 2 is an end view of the stabilized spine electrode assembly shown in FIG. 1.

An end view of the stabilized spine electrode assembly 16 shown in FIG. 1 is schematically depicted in FIG. 2. In this embodiment, tethers 24 may have substantially equal lengths to provide an even radial distribution of spines 18. Alternatively, the lengths of tethers 24 may be adjusted to provide any desired distribution of spines 18. As will be appreciated, the tethers 24 secured to the adjacent spines apply tensions that have radial and axial vectors. The radial vectors are generally opposing for the intermediate spine, thereby stabilizing it against undesired radial movement with respect to its adjacent spines. This configuration exists whenever a given spine has two separate adjacent spines, and therefore applies to embodiments employing three or more spines 18. However, even embodiments employing two spines 18 are stabilized, as the spines are constrained against movement away from each other by tether 24.

Figure 3:
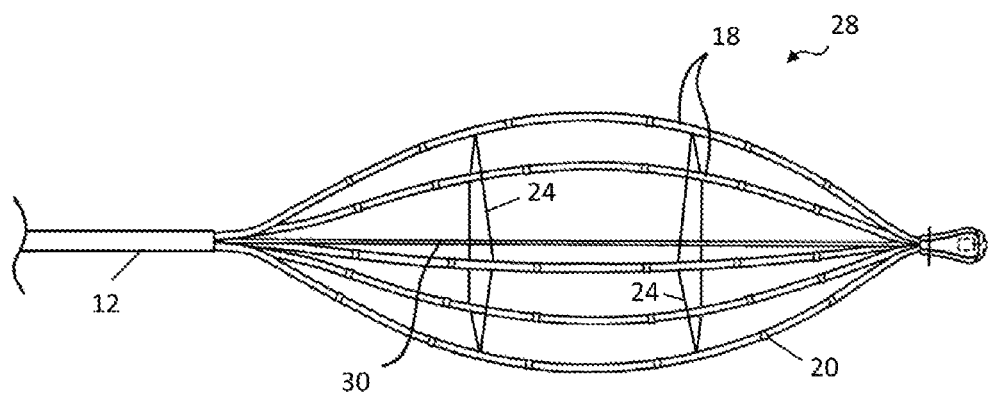
FIG. 3 is a schematic view of a basket-shaped stabilized spine electrode assembly, according to one embodiment.

Another suitable embodiment is depicted in FIG. 3, which shows stabilized spine electrode assembly 28 configured as a basket-shaped electrode assembly at the distal end of catheter body 12. As shown, each spine 18 is secured to each other at their proximal and distal ends. In this embodiment, the distal ends of spines 18 are secured to puller wire 30 which runs to the proximal end of catheter 10. Further, two tethers 24 are secured between adjacent spines 18, however any desired number of tethers 24 may be employed. For example, a single tether 24 between each pair of spines 18 may be used, with stability maximized when the single tether is positioned equatorially, within an intermediate third of the length of spine, such as at a midpoint. Alternatively, the single tether may be moved proximally or distally to impart greater or lesser stability characteristics to the respective poles of stabilized spine electrode assembly 28. As another example, three or more tethers 24 may be provided between each adjacent pair of spines 18. By manipulating puller wire 30 to move it longitudinally in the proximal direction, the relative distance between the distal and proximal ends of spines 18 is shortened, causing them to bow outwards into the expanded arrangement. As such, the radial diameter of stabilized spine electrode assembly 18 may be adjusted based on the amount puller wire 30 is moved. In such embodiments, tethers 24 may be formed from a compliant material as noted above. Alternatively, spines 18 may have a preshaped configuration when not restrained by a guiding sheath, causing them to expand radially outwards to assume the expanded arrangement. The puller wire may be used to further adjust the configuration or may be omitted as desired.

Figure 4:
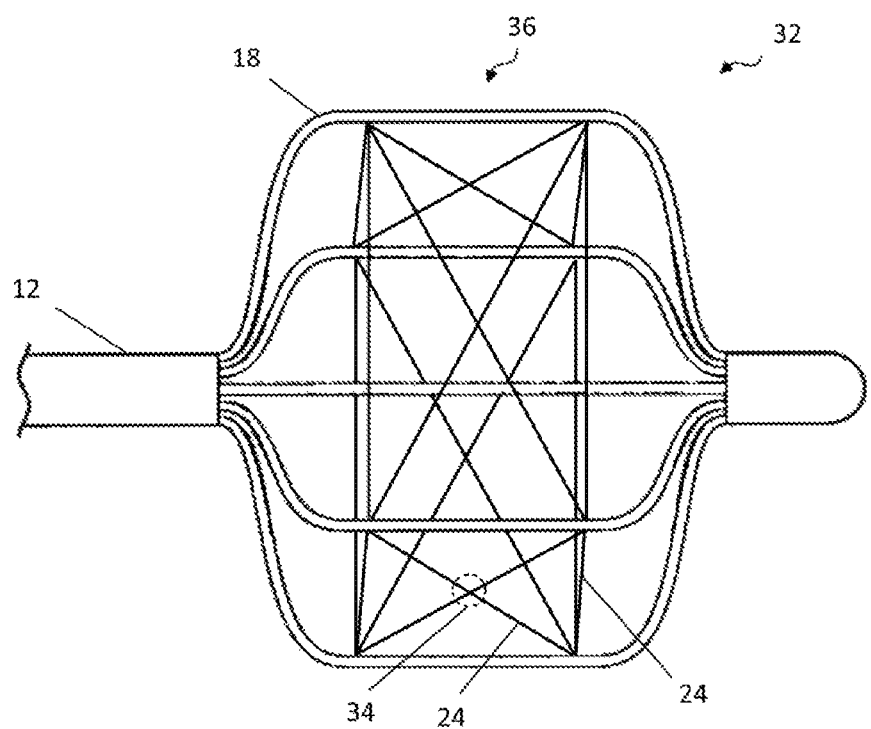
FIG. 4 is a schematic view of a basket-shaped stabilized spine electrode assembly, according to another embodiment.

Yet another configuration is depicted in the embodiment shown in FIG. 4, with stabilized spine electrode assembly 32 also configured as a basket-shaped electrode assembly at the distal end of catheter body 12. The spine arrangement and configuration of stabilized spine electrode assembly 32 may be similar to that described with respect to FIG. 3. In this embodiment, multiple tethers 24 are employed between adjacent pairs of spines 18. Notably, for a given attachment point, two tethers 24 extend to each adjacent spine 18. Two tethers 24 extend to attachment points on the adjacent spines that have a corresponding relative longitudinal position and two tethers 24 extend to attachment points at different relative longitudinal positions. In this manner, a web of tethers 24 may be established between adjacent spines 18 to further stabilize them. If desired, two tethers may be secured together when they cross between adjacent spines 18, such as at junction 34. In the embodiment shown, tethers 24 may be formed from a relatively noncompliant material to help stabilized spine electrode assembly 32 assume a desired expanded arrangement. As shown, an intermediate portion 36 of each spine 18 is held relatively parallel to the longitudinal axis of catheter 10 by the use of multiple tethers 24 between adjacent spines. Accordingly, longitudinal movement of puller wire 30 that causes spines 18 to bow outwards produces an expanded arrangement with a flattened equatorial region. Other attachment points and patterns of tethers 24 may be employed to impart expanded arrangements having other shapes as desired.

As noted, the struts or other structural supports used to form spines 18 may be configured to assume the expanded and collapsed arrangements and may comprise a shape memory material in some embodiments. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature.

The temperature at which nitinol has finished transforming to austenite upon heating is referred to as the "Af" temperature. Accordingly, stabilized spine electrode assembly 16 may have a three dimensional shape that can be easily collapsed to be fed into a guiding sheath and then readily returned to its expanded shape memory configuration upon delivery to the desired region of the patient upon removal of the guiding sheath.

Figure 5:
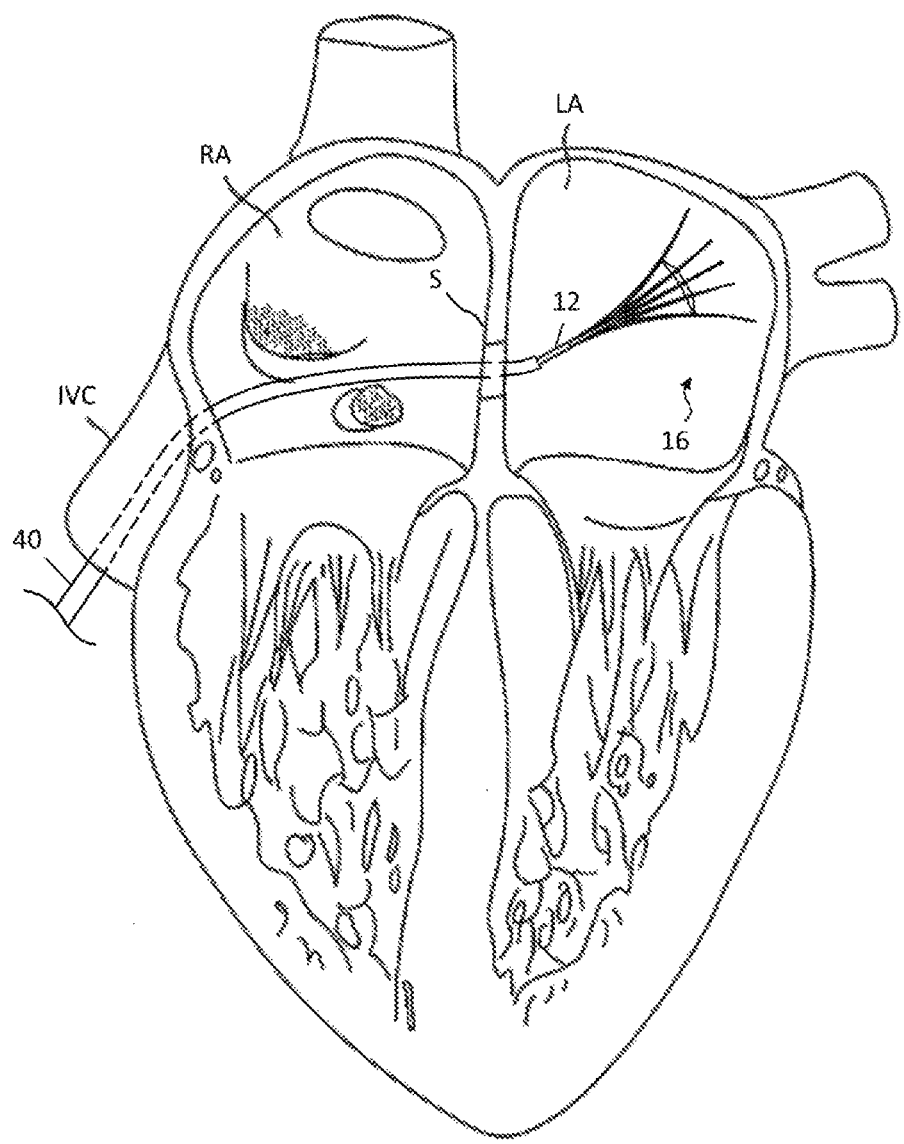
FIG. 5 is a schematic view of a stabilized spine electrode assembly positioned within the left atrium, according to one embodiment.

In one aspect, an electrophysiologist may introduce a guiding sheath, guidewire and dilator into the patient, as is generally known in the art. As an example, a guiding sheath for use in connection with the inventive catheter is an appropriately-sized PREFACE™ Braided Guiding Sheath (commercially available from Biosense Webster, Inc., Diamond Bar, Calif.). The guidewire is inserted, the dilator is removed, and the catheter is introduced through the guiding sheath whereby the guidewire lumen in the expander permits the catheter to pass over the guidewire. In one exemplary procedure as depicted in FIG. 5, the catheter is first introduced to the patient's heart (H) through the right atrium (RA) via the inferior vena cava (IVC), where it passes through the septum (S) in order to reach the left atrium (LA).

As will be appreciated, stabilized spine electrode assembly 16 may be deflected into a straightened configuration and constrained within guiding sheath 40 to allow catheter 10 to be passed through the patient's vasculature to the desired location. Once the distal end of the catheter reaches the desired location, e.g., the left atrium, guiding sheath 40 is withdrawn to expose the stabilized spine electrode assembly 16, allowing it to assume the expanded arrangement, with tethers 24 stabilizing spines 18 in an intended configuration. Depending on the embodiment, a puller wire or other suitable control mechanism may be manipulated to facilitate assumption of the expanded arrangement.

Figure 6:
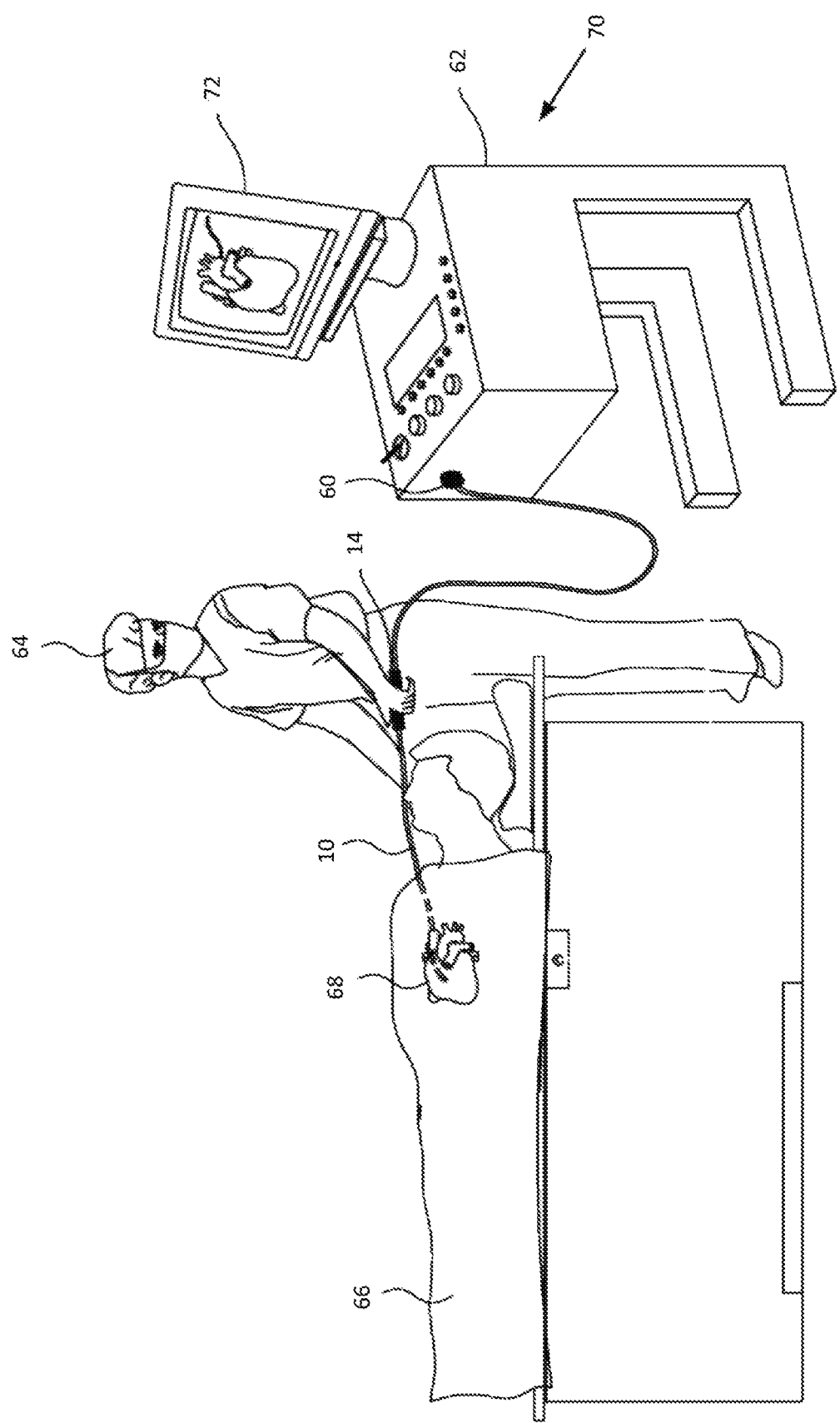
FIG. 6 is a schematic illustration of an invasive medical procedure using a stabilized spine electrode assembly, according to one embodiment.

As will be appreciated, a procedure employing a stabilized spine electrode assembly with the techniques of this disclosure allow any desired operation involving measuring electrical signals and/or ablating tissue within a patient. To help illustrate use of the stabilized spine electrode assembly 16, FIG. 6 is a schematic depiction of an invasive medical procedure, according to an embodiment of the present invention. Catheter 10, with the stabilized spine electrode assembly 16 (not shown in this view) at the distal end may have a connector 60 at the proximal end for coupling the leads of the electrodes and sensors (not shown in this view) to a console 62 for recording and analyzing the signals they detect as well as for supplying ablating energy. An electrophysiologist 64 may insert the catheter 10 into a patient 66 in order to acquire electropotential signals from the heart 68 of the patient. The electrophysiologist 64 uses the control handle 14 attached to the catheter in order to perform the insertion. Console 62 may include a processing unit 70 which analyzes the received signals, and which may present results of the analysis on a display 72 attached to the console. The results are typically in the form of a map, numerical displays, and/or graphs derived from the signals. Processing unit 70 may also control the delivery of energy to electrode 24 for creating one or more lesions, such as at locations associated with abnormal electrical activity identified by analyzing received signals.

Further, the processing unit 70 may also receive signals from position sensors, such as sensor 26 (not shown in this view). As noted, the sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the stabilized spine electrode assembly 16 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally with respect to stabilized spine electrode assembly 16. The coordinates of the distal sensor relative to the proximal sensor may be determined and, with other known information pertaining to the configuration of stabilized spine electrode assembly 16, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated catheter body having a proximal end, a distal end; and
    a stabilized spine electrode assembly mounted at the distal end of the catheter body and comprising at least two spines and at least two tethers, each spine having at least one electrode and a proximal end attached at the distal end of the catheter body, wherein the at least two tethers are secured to one location on one spine and to a plurality of locations on an adjacent spine and are secured between locations distal of the proximal ends of adjacent spines and wherein each spine has a collapsed arrangement in which the spines are arranged generally along a longitudinal axis of the catheter body and an expanded arrangement in which at least a portion of each spine bows radially outwards from the longitudinal axis and the at least two tethers exert tension on the adjacent spines, the stabilized spine electrode assembly being further configured to move from a first expanded configuration to a second expanded configuration when in the expanded arrangement.

2. The catheter of claim 1, wherein the stabilized spine electrode assembly further comprises at least three spines, wherein the at least two tethers are secured to locations distal of the proximal ends of at least one spine and each adjacent spine.

3. The catheter of claim 2, wherein the at least two tethers are configured to maintain a desired radial distribution of the spines relative to each other when in the expanded arrangement.

4. The catheter of claim 3, wherein the at least two tethers are configured to maintain an even radial distribution of the spines relative to each other when in the expanded arrangement.

5. The catheter of claim 2, wherein the at least three spines have distal ends and are secured to each other at the distal ends to form a basket-shaped electrode assembly.

6. The catheter of claim 5, wherein the at least two tethers are secured between equatorial locations of the spines.

7. The catheter of claim 1, wherein the at least two tethers are secured to a proximal third of a spine.

8. The catheter of claim 1, wherein the at least two tethers are secured to an intermediate third of a spine.

9. The catheter of claim 1, wherein the at least two tethers are secured to a distal third of a spine.

10. The catheter of claim 1, wherein the at least two tethers comprise a polymeric fiber.

11. The catheter of claim 10, wherein the at least two tethers are compliant.

12. The catheter of claim 10, wherein the at least two tethers are relatively noncompliant.

13. The catheter of claim 1, wherein each spine comprises at least two longitudinally spaced tether attachment points.

14. The catheter of claim 13, wherein each spine further comprises an intermediate spine portion located between the at least two longitudinally spaced tether attachment points, the intermediate spine portion being held substantially parallel to the longitudinal axis of the catheter body when the stabilized spine electrode assembly is in the expanded arrangement.

15. A method for treatment comprising:
providing a catheter with an elongated catheter body having a proximal end, a distal end and a stabilized spine electrode assembly mounted at the distal end of the catheter body and comprising at least two spines and at least two tethers, each spine having at least one electrode and a proximal end attached at the distal end of the catheter body, wherein the at least tethers are secured to one location on one spine and to a plurality of locations on an adjacent spine and are secured between locations distal of the proximal ends of adjacent spines;
advancing the distal end of the catheter with the stabilized spine electrode assembly to a desired region within a patient with each spine in a collapsed arrangement in which the spines are arranged generally along a longitudinal axis of the catheter body; and
causing the stabilized spine electrode assembly to assume an expanded arrangement in which at least a portion of each spine bows radially outwards from the longitudinal axis and the at least two tethers exerts tension on the adjacent spines so that at least one electrode is in contact with tissue, the stabilized spine electrode assembly being further configured to move from a first expanded configuration to a second expanded configuration when in the expanded arrangement.

16. The method of claim 15, further comprising receiving electrical signals from the at least one electrode in contact with tissue.

17. The method of claim 15, further comprising delivering radio frequency energy to the at least one electrode in contact with tissue to form a lesion.

* * * * *